(12) United States Patent
Hoogerhout

(10) Patent No.: US 6,361,777 B1
(45) Date of Patent: Mar. 26, 2002

(54) METHOD OF COUPLING POLYSACCHARIDES TO PROTEINS

(75) Inventor: Peter Hoogerhout, Bilthoven (NL)

(73) Assignee: De Staat der Nederlanden,vertegenwoordigd door de minister Van Welzijn, volksgezondheid en Cultuur, Rijswijk (NL)

( * ) Notice: Subject to any disclaimer, the term of this patent is extended or adjusted under 35 U.S.C. 154(b) by 0 days.

(21) Appl. No.: 09/331,029

(22) PCT Filed: Dec. 16, 1997

(86) PCT No.: PCT/NL97/00700

§ 371 Date: Aug. 16, 1999

§ 102(e) Date: Aug. 16, 1999

(87) PCT Pub. No.: WO98/27107

PCT Pub. Date: Jun. 25, 1998

(30) Foreign Application Priority Data

Dec. 16, 1996 (EP) .............................. 96203556

(51) Int. Cl.[7] ........................ A61K 39/385; C07K 9/00; C07K 1/00; C07H 1/00
(52) U.S. Cl. ................. 424/193.1; 424/184.1; 514/25; 530/300; 530/322; 530/350; 530/395; 536/123.1; 536/124
(58) Field of Search .............................. 536/123.1, 124; 530/395, 322, 300, 350; 424/184.1, 193.1; 514/25

(56) References Cited

FOREIGN PATENT DOCUMENTS

WO WO9611709 4/1996

OTHER PUBLICATIONS

A F M Verheul et al.: "Preparation . . . etc." Infection and Immunity, vol. 59, No. 3, Mar. 1991, Washington U.S, pp. 843–851.

Chemical Abstracts, vol. 126, No. 13, Mar. 25, 1997, abstract No. 171807.

Chemical Abstracts, vol. 118, No. 11, Mar. 15, 1993, abstract No. 102358.

Biological Abstracts, vol. 87, 1987, abstract No. 167721.

*Primary Examiner*—Elli Peselev
(74) *Attorney, Agent, or Firm*—Handal & Morofsky

(57) ABSTRACT

A novel method of covalently coupling polysaccharides to other biopolymers is provided, using an amino-thiol linker represented by formula (1): $H_2N-[(CH_2)_m-CHR^1-CR^2R^3-A]_q-CHR^4-(CHR^5)_p-CHR^6-S-R^7$ wherein A is a direct bond or a group having the formula $-\{Z-(CH_2)_m-CHR^1-CHR^2R^3\}_n Z-$, m is an integer form 0 to 5; n is an integer form 0 to 3; p is an integer from 0 to 2; q is the integer 0 or 1; $R^1$ is hydrogen or $C_1-C_6$ alkyl, optionally substituted by amino, hydroxyl, carboxyl, $C_1-C_4$ alkoxycarbonyl, carbamoyl, mono- or di($C_1-C_4$alkyl) carbamoyl or N-(α-carboxyalkyl)carbamoyl, or, if m ≠0, $R^1$ is hydroxyl, amino or peptidylamino; $R^2$ and $R^3$ are independently hydrogen or $C_1-C_4$ alkyl, or together from an oxo group; $R^4$ is hydrogen, $C_1-C_4$ alkyl, carboxyl, $C_1-C_4$ alkoxycarbonyl, carbamoly, mono-or di($C_1-C_4$ alkyl) carbamoyl or N-(α-carboxyalkyl) carbamoyl; $R^5$ is hydrogen, methyl, hydroxy or $C_1-C_7$ acyloxy; $R^6$ is hydrogen or methyl; $R^7$ is hydrogen or thiol-protecting group or group having the formula $-S-CHR^6-(CHR^5)_p-CHR^4-[A-CR^2R^3-CHR^1-(CH_2)_m]_q-NH_2$; and Z is imino, methylimino, oxygen or sulphur.

26 Claims, No Drawings

METHOD OF COUPLING POLYSACCHARIDES TO PROTEINS

The present invention relates to the use of aminothiol compounds as linkers in preparing conjugate vaccines.

Covalent binding of a polysaccharide or other hapten to an immunogenic protein or peptide or other bio-organic molecule has proven to be a suitable method of preparing effective vaccines, for example against pathogenic organisms such as *Haemophilus influenzae* type b (meningitis, otitis media), *Bordetella pertussis* (whooping cough), *Clostridium tetani* (tetanus), meningococci (*Neisseria meningitidis*, meningitis, otitis media) and pneumoccocci (*Streptococcus pneumoniae*, pneumonia, meningitis, otitis media). Such conjugate vaccines have been described e.g. in U.S. Pat. No. 4,762,713. According to this US patent, binding between the polysaccharide and the carrier protein is performed by reductive amination of aldehyde or hemiacetal functions of the poly-saccharides with amino groups in the protein. Another suitable method of covalently binding a polysaccharide to a proteinaceous material is by activating hydroxyl functions to produce a side chain containing a function that can be coupled to the protein. Thus, the polysaccharide can be activated and then coupled to a thiol-bearing group such as cysteamine, which can be coupled to an activated amino acid in the protein. The use of cysteamine for coupling oligosaccharides to proteins has been described by Verheul et al (*Infect. Immun.* 59 (1991) 843–851). This use comprises activation of the saccharide by converting a carboxylic group to an N-succinimidyl ester (NSu), according to the following scheme:

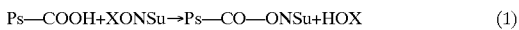  (1)

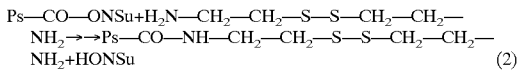  (2)

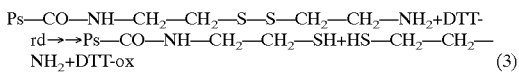  (3)

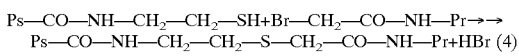  (4)

wherein Ps represents a polysaccharide, Pr represents a protein or peptide, and DTT-rd represents dithiothreitol in its reduced (dithiol) form and DTT-ox in its oxidised (1,2-dithiane) form. This approach, however, requires the presence of carboxyl groups in the polysaccharide, while many biologically interesting polysaccharides do not contain a carboxyl group.

It was found that polysaccharides can be effectively bound to cysteamine-like linkers without the need of other functional being present than hydroxyl groups by cyanogen bromide activation according to the following scheme.

  (5)

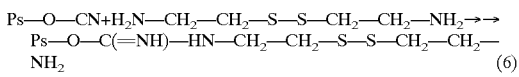  (6)

Reaction (5) is followed by side reactions including a reaction with a second hydroxyl group to produce a cyclic imidocarbonate which can also result in coupling with an amino group as in reaction (6).

Thus the invention relates to a method of coupling a polysaccharide to another biopolymer wherein the polysaccharide is activated with a cyananting agent such as cyanogen halide and the activated polysaccharide is reacted with and aminothiol linker having formula 1

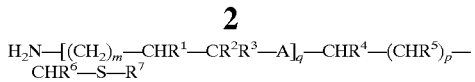

wherein

A is a direct bond or a group having the formula

m is an integer from 0 to 5;

n is an integer from 0 to 3;

p is an integer from 0 to 2;

q is the integer 0 or 1;

$R^1$ is hydrogen or $C_1$–$C_6$ alkyl, wherein the $C_1$–$C_6$ alkyl is optionally substituted by amino, hydroxyl, carboxyl, $C_1$–$C_4$ alkoxycarbonyl, carbamoyl, mono- or di-$C_1$–$C_4$-alkylcarbamoyl or N-(α-carboxyalkyl) carbamoyl-; or if m ≠0, $R^1$ is hydroxyl, amino or peptidyl-amino;

$R^2$ and $R^3$ are independently hydrogen or $C_1$–$C_4$ alkyl, or together from an oxo group;

$R^4$ is hydrogen, $C_1$–$C_4$ alkyl, carboxly, $C_1$–$C_4$ alkoxycarbonyl, carbamoly, mono-or di-$C_1$–$C_4$-alkylcarbamoyl or N-(α-carboxyalkyl) carbamoyl;

$R^5$ is hydrogen, methyl, hydroxy or $C_1$–$C_7$ acyloxy;

$R^6$ is hydrogen or methyl;

$R^7$ is hydrogen or thiol-protecting group or group having the formula

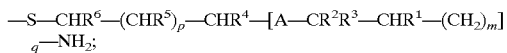

and

Z is imino, methylimino, oxygen or sulphur;

to produce a thiolated polysaccharide having the formula 2

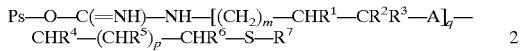  2 wherein Ps represents a polysaccharide residue and A, m, p, q, $R^1$, $R^2$, $R^3$, $R^4$, $R^5$, $R^6$ and $R^7$ are as defined above, followed by optionally removing protecting group $R^7$ and reacting the thiolated polysaccharide with an activated biopolymer. The preferred linkers are as defined in claims 3–8. A suitable example of the linkers is cysteamine or its oxidised form cystamine.

This method works satisfactorily for the majority of polysaccharides including most bacterial polysaccharides. However, no coupling to a useful degree is found with some polysaccharides such as the 19F type pneumococcal capsular polysaccharide.

Although the present inventors do not wish to be bound by any specific theory, one possible explanation for the incompleteness or failure of the cysteamine coupling is that the cysteamine adduct, once formed, may revert to the original materials by intramolecular displacement.

It has furthermore been found that any insufficient coupling can be solved by using amino-thiol linkers complying with formula 3,(=formula 1 with q=1)

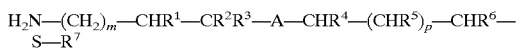

wherein

A is a direct bond or a group having the formula

m is an integer from 0 to 5;

n is an integer from 0 to 3, preferably between 0 and 2;

p is an integer from 0 to 2;

q is the integer 0 or 1;

$R^1$ is hydrogen or $C_1$–$C_6$ alkyl, wherein the $C_1$–$C_6$ alkyl is optionally substituted by amino, hydroxyl, carboxyl, $C_1$–$C_4$ alkoxycarbonyl, carbamoyl, mono- or di-$C_1$–$C_4$-alkylcarbamoyl or N-(α-carboxyalkyl) carbamoyl; or, if m≠0, $R^1$ is hydroxyl, amino or peptidyl-amino;

$R^2$ and $R^3$ are independently hydrogen or $C_1$–$C_4$ alkyl, or together from an oxo group;

$R^4$ is hydrogen, $C_1$–$C_4$ alkyl, carboxly, $C_1$–$C_4$ alkoxycarbonyl, carbamoly, mono-or di-$C_1$–$C_4$-alkylcarbamoyl or N-(α-carboxyalkyl) carbamoyl;

$R^5$ is hydrogen, methyl, hydroxy or $C_1$–$C_7$ acyloxy;

$R^6$ is hydrogen or methyl;

$R^7$ is hydrogen or thiol-protecting group or group having the formula

—S—CHR$^6$—(CHR$^5$)$_p$—CHR$^4$—[A—CR$^2$R$^3$—CHR$^1$—(CH$_2$)$_m$]$_q$—NH$_2$;

and

Z is imino, methylimino, oxygen or sulphur, wherein $R^2$ and $R^3$ together can form an oxo group.

The amino-thiol linkers according to formula 3 may be straight or branched α,ω-aminothiol derivatives having at least 4 carbon atoms and optionally one or more heteroatoms in the chain, such as 4-aminobutanethiol, 5-aminopentanethiol, 2-(2-aminoethylaminoethanethiol and the like. Preferred compounds are those wherein H$_2$N—(CH$_2$)$_m$—CHR$^1$—CR$^2$R$^3$— represents an amino acid such as glycine, alanine, β-alanine, serine, glutamine, γ-aminobutyric acid, lysine and ε-aminocaproic acid, or an oligopeptide such as Nα-glycyl-lysine and higher homologues of Nα-peptidyl-α,ω-diaminoacids. The group H$_2$N—(CH$_2$)$_m$—CHR$^1$—CR$^2$R$^3$—A— may also represent a linear oligopeptide such as glycylglycine.

In the linkers of both formula 1 and 3, the group A—CHR$^4$—(CHR$^5$)$_p$—CHR$^6$—S—R$^7$ may e.g. be derived from 2-aminoethanethiol (cysteamine), 2-mercaptoethanol, 1,2-ethanedithiol, 2-amino-2-methylpropanethiol, 3-aminopropanethiol, 2-hydroxy-3-aminopropanethiol, monothio- and dithio-threitol or -erythritol, cysteine, homocysteine and their esters or amides, and the like. The most preferred compounds according to formula 3 are N-glycyl-cysteamine and its disulphide precursor N,N'-diglycyl-cystamine.

Most of the compounds complying with formula 1 and 3, such as N,N'-di-glycylcystamine and N-alanyl-S-acetylcysteamine, are known from WO 85/00167 as radioprotective agents.

Biopolymers that can be conjugated by the present process comprise any macro-molecular (MW>1 kDa) natural or nature-like compound containing hydroxyl, amino and/or mercapto groups. In particular, such biopolymers include natural or modified polysaccharides, natural, modified or synthetic peptides and proteins, lipoproteins, glycoproteins and nucleic acids. Most preferably the present linkers are used for conjugating one or more polysaccharides to a protein or peptide.

Polysaccharides that can be conjugated include starch-like and cellulosic material, but the present method is especially suitable for conjugating microbial polysaccharides that are haptens or immunogens. Examples thereof are pneumococcal capsular polysaccharides of the various types including e.g. Danish types 1, 3, 4, 6A, 6B, 7S, 9V, 14, 18C, 19F and 23F, group B streptococcal polysaccharides, capsular polysaccharides of *Klebsiella pneumoniae*, *Haemophilus influenzae* including type b polysaccharide, *Neisseria meningitidis* (groups A and C), *Pseudomonas aeruginosa* or *Escherichia coli*. It is noted that the term "polysaccharides" as used herein comprises sugar-containing polymers and oligomers, whether they only contain glycosidic linkages or also phosphodiester or other linkages. They may also contain non-sugar moieties such as acid groups, phosphate groups, amino groups, sugar alcohols and amino acids, and they may be depolymerised or not. By way of illustration the repeating units of the pneumococcal capsular polysaccharides types 6B, 14, 19F and 23 and the *H. influenzae* type b capsular polysaccharide are given below:

Pn 6B →2)-α-D-Galp-(1→3)-α-D-Glcp-(1→3)-α-L-Rhap-(1→4)-D-Ribitol -5-(PO$_4^-$→

Pn 14 →4)-β-D-Glcp-(1→6)-β-D-Glcp*NAc-(1→3)-β-D-Galp-(1→

*: bearing a β-D-Galp-(1→4) side group

Pn 19F →4)-β-ManpNAc-(1→4)-α-D-Glcp-(1→2)-α-L-Rhap-(1-PO$_4^-$→

Pn 23F →4)-β-D-Glcp$^\#$-(1→4)-β-D-Galp$^\&$-(1→4)-β-L-Rhap-(1→

$^\#$: bearing a phosphoglyceryl-(→3) side group $^\&$: bearing an α-L-Rhap-(1→2) side group Hi b →3)-β-D-Ribf-(1→1)-D-Ribitol-5-(PO$_4^-$→

A review of bacterial polysaccharides of interest can be found in: Lennart Kenne and Bengt Lindberg, "Bacterial polysaccharides" in *The polysaccharides*, Vol. 2, Ed. G. O. Aspinall, 1983, Ac. Press, pp. 287–363.

Proteins and peptides that may be conjugated with the present method include immunogenic and non-immunogenic proteins. Examples are serum albumins and various bacterial toxins and toxoids, such as diphtheria toxin, tetanus toxoid, pneumolysin, pneumolysoid, toxins of other organisms such as Pseudomonas, Staphylococcus, *Bordetella pertussis*, *Escherichia coli*, optionally detoxified, so-called cross-reacting material (e.g. CRM 197) and haemocyanins. They may also be outer membrane proteins of organisms such as *Neisseria meningitidis* or *Bordetella pertussis*. The proteins may also be antibodies to be used for conveying another biomaterial to a desired site. The proteins and peptides may be used as independent immunogens, or they may be used to render the other material such as haptens more immunogenic. They may native or detoxified or mutated. The term peptides and proteins are used indiscriminately herein, even though proteins in general denote higher molecular weight materials than peptides.

The linkers of formula 3 can be prepared by methods known per se, such as those described in EP-A-131500. For example, the linker compound can be prepared from a suitable amino-thiol, dithiol or mercapto-alcohol, according to the nature of group A, such as 2-aminoethanethiol (cysteamine), 3-aminopropanethiol or cysteine, wherein the thiol group is preferably protected e.g. by an acyl group or as a disulphide. If the group A contains a chain with the formula —(Z—CHR$^1$—CHR$^2$R$^3$)$_n$—, this can be introduced by reaction with e.g. ethyleneimine, propylene oxide, under the appropriate conditions to obtain an adduct having the desired value of n. Alternatively, if 13 (Z—CHR$^1$—CHR$^2$R$^3$)$_n$— represents an oligopeptide chain, this group can be introduced by conventional peptide synthesis methods. The terminal group H$_2$N—(CH$_2$)$_m$—CHR$^1$—CR$^2$R$^3$— can be introduced by reaction of the appropriate-activated compound with the precursor HA—CHR$^4$—(CHR$^5$)$_p$—CHR$^6$—S—R$^7$. Where H$_2$N—(CH$_2$)$_m$—CHR$^1$—CR$^2$R$^3$— represents an amino acid residue such as glycine, alanine or lysine, it can be coupled again by conventional methods.

The use of the amino-thiol linkers comprises coupling of the linker, preferably with a protecting group on the thiol function, to a first biopolymer, especially a polysaccharide, which is optionally activated. Activation can be performed using known methods, such activation of a carboxyl groups on the polysaccharide (if present) e.g. with a carbodiimide, or by introduction of an aldehyde group, e.g. by oxidation. Advantageously, coupling is performed by reaction with cyanogen bromide. This results in the presence of reactive isocyanate groups, which readily react with the amino function of the linker to produce an isoureum bond. The CNBr activation is performed in such a manner that at least 0.1 activated site is introduced per repeating unit (RU) (in a polysaccharide: a repeating mono- or oligosaccharide unit). The coupling preferably yields 1 amino function per 1–10 RU.

The thiol-protecting group, if present, is then removed e.g. by reaction of the protecting disulphide with a reducing agent, for example a mercaptan such as 2-mercaptoethanol or dithiothreitol, or a trialkylphosphine. Reduction preferably results in 1 thiol group per 5–15 RU. The thiol function can then react with an active function of a second biopolymer, such as a bromoacyl group, an iodoacyl group, a pyridyldithio group or a maleimido-alkyl (or -aryl or -cycloalkyl) group, preferably bound to a lysine residue of the protein. The activated function can be introduced by chemical post-modification of the protein, such as reaction with N-succinimidyl-bromoacetate or N-(ω-maleimidoalkyloxy)succinimide, or by peptide synthesis using one or more amino acid precursors already containing the active function.

The intermediates and the final conjugate can be purified as necessary using methods known per se, such as chromatography (ion exchange, hydrophobic interaction or affinity), gel filtration, dialysis, membrane filtration, selective precipitation using ammonium sulphate or alcohol, and the like.

The conjugates can be incorporated in a vaccine formulation in a manner known in the field of vaccination, using appropriate adjuvants, diluents, stabilisers, buffers, etc. The vaccines can be used in protecting humans against pathogens or in protecting animals. Alternatively the conjugates of appropriate biopolymers can be used in human or veterinary therapy or as a diagnostic agent.

Another advantageous use of the method of the present invention concerns immobilisation of proteins and peptides on a polysaccharide such as dextrans agarose, sepharose for the purpose of purification of antigens, antibodies and other biologically relevant molecules e.g. by affinity chromatography, or for use in immunoassays and the like.

EXAMPLES

The following abbreviations are used in the examples

| | |
|---|---|
| Boc | tert-butyloxycarbonyl |
| BrAc | bromoacetyl |
| DTE | dithioerythritol |
| EDTA | ethylenediaminetetraacetic acid |
| Gly | glycyl |
| GP(C) | gel permeation (chromatography) |
| HPLC | high-performance liquid chromatography |
| m.w. | molecular weight |
| NSu | N-succinimidyl |
| ONSu | N-oxysuccinimidyl |
| PBS | phosphate-buffered saline, 10 mM sodium phosphate in physiological salt, pH 7.2 |
| Pn | pneumococcus/pneumococcal |
| PS | polysaccharide |
| RP | reverse phase |
| RU | repeating unit(s) of the polysaccharide |
| TNBS | trinitrobenzenesulphonic acid |
| TTd | tetanus toxoid |

Note: the Danish nomenclature for pneumococcal serotype classification is used; the American type is mentioned within brackets.

Example 1

Preparation of a Linker

N,N'-Bis[tert-butyloxycarbonylglycyl]cystamine (N,N'-bis[Boc-Gly]cystamine)

N,N-Dimethylacetamide (42 ml) and N,N-diisopropylethylamine (14.6 ml, 83.8 mmol) were added to a mixture of N'-succimmidyl N-(tert-butyloxycarbonyl) glycinate, Boc-Gly-ONSu, (11.4 g, 41.9 mmol) and cystamine dihydrochloride (3.77 g, 16.7 mmol). The suspension was stirred overnight at room temperature (cystamine dihydrochloride dissolved gradually in a few hours). The clear solution was diluted with water (16.7 ml), which caused phase separation. After stirring for 1 h, diethyl ether (170 ml) was added and the mixture obtained was washed with water (170 ml). After phase separation, the water layer was extracted with diethyl ether (85 ml). The organic phases were combined, washed with 1 M NaHCO$_3$ (3×85 ml), water (3×85 ml) and 1 M NaH$_2$PO$_4$ (3×85 ml), successively, and dried with MgSO$_4$. The MgSO$_4$ was removed by filtration and the filtrate was concentrated in vacuo to give N,N'-bis[Boc-Gly]cystamine (4.81 g, 62%) as a glassy solid. RP-HPLC shows a single sharp peak.

N,N'-bisglycylcystamine (bistrifluoroacetate)

N,N'-bis[Boc-Gly]cystamine (4.81 g, 10.3 mmol), as obtained in the previous step, was dissolved in dichloromethane (16.7 ml). The solution was stirred and trifluoroacetic acid (16.7 ml) was added. Formation of isobutene and carbon dioxide was visible for about 5 min. After a total period of 30 min, the reaction mixture was added dropwise to a powerfully stirred mixture of diethyl ether (170 ml) and pentane (170 ml). Stirring was ended and the precipitate was allowed to settle for 5 min. Diethyl ether/pentane was removed by decantation and the solid was washed with a mixture of diethyl ether (50 ml) and pentane (50 ml). Again, diethyl ether/pentane was removed by decantation. The hygroscopic solid was dissolved in water (40 ml). Traces of diethyl ether/pentane were removed in vacuo at room temperature. Thereafter, the solution was lyophilised to give N,N'-bisglycylcystamine bistrifluoroacetate (4.93 g, 97%). Finally, the compound was dissolved in water at a concentration of 1.0 M and stored frozen at −20° C. RP-HPLC shows a single sharp peak.

Example 2

Preparation of Pn PS 19F/TTd Conjugate Vaccine Using N,N'-bisglycylcystamine

Partial depolymerisation of Pn PS 19F

For the partial depolymerisation of pneumococcal polysaccharide, a sonication process was used. Pneumococcal polysaccharide serotype 19F (American type 19, RIVM, lot. no. 19FEXP2A/S13; 275 mg, dry weight), was dissolved in 20 ml water and sonicated in periods of ~15 min, for a total of 125 min, with a ¼" microtip (Branson Sonifier 250, output level 7, 50% duty cycle). The m.w. of the PS was reduced from ~980 to 49 kDa (from ~1660 to ~83 RU). The solution was filtered over an 0.45 µm membrane with 94% recovery of PS (anthrone assay).

Modification of Pn PS 19F (49 kD) with N,N'-bisglycylcystamine

For the modification, 3.25 ml of PS 19F solution in water (6.15 mg/ml) was mixed with an equal volume of 1 M sodium carbonate solution (pH ~12). The mixture was cooled to ~2° C. While stirring, 250 µl CNBr reagent (100 mg/ml in acetonitrile) was added. After 10 minutes, the solution was subjected to gel filtration over Sephadex G25M (Pharmacia) at ~4° C. (eluent: 0.2 M sodium carbonate-bicarbonate buffer pH 9.25). The PS-containing fraction was mixed with 4.73 ml of a pre-cooled solution of 0.2 M sodium carbonate-bicarbonate buffer pH 9.25/1.0 M N,N'-bisglycylcystamine (bis-trifluoroacetate), 1/1, v/v. The pH dropped to 6.5, and was re-adjusted to 9.3 with 6 M sodium hydroxide. In the course of 1.5 h, the pH was checked occasionally and—if necessary—re-adjusted. Thereafter, the mixture was kept at ~4° C. overnight. Finally, the sample was buffer-exchanged against 0.1 M sodium phosphate buffer, containing 5 mM EDTA, pH 8, and concentrated to a volume of 2 ml on a Centriprep-10 (Amicon) concentrator. Analysis of primary amino groups gave 1 $NH_2$/4.2 RU (TNBS assay).

Reduction of N,N'-bis[glycyl]cystamine-modified Pn PS 19F

N,N'-bis[glycyl]cystamine-modified Pn PS 19F (13 mg in 1.75 ml 0.1 M sodium phosphate buffer, containing 5 mM EDTA, pH 8) was reduced by adding an 11-fold molar excess of DTE (based on the number of amino groups introduced into the PS). After incubation overnight at room temperature, the sample was subjected to gel filtration over Sephadex G25M (Pharmacia) using 0.1 M sodium phosphate buffer, containing 5 mM EDTA, pH 7, as the eluent and concentrated to a volume of 3.5 ml on a Centriprep-10. Analysis for sulphydryl groups gave 1 SH/8.5 RU (Ellman assay).

Bromoacetylation of Tetanus Toxoid

Tetanus toxoid (RIVM) was buffer-exchanged by gel filtration over Sephadex G25M (eluent: 0.1 M sodium phosphate buffer, containing 5 mM EDTA, pH 8). Amino groups of side-chains of lysine in the protein were modified by adding a 6-fold excess (based on the number of lysines within TTd) of N-succinimidyl bromoacetate. The mixture was incubated for 1.5 h at room temperature and loaded onto a column of Sephadex G25M (eluent: 0.1 M sodium phosphate buffer, containing 5 mM EDTA, pH 7). Analysis of the protein-containing fraction showed that 40% of the amino groups (initial amount: 33.5 $NH_2$ per mol TTd) had been modified (TNBS assay).

Conjugation of N-(glycyl)cysteamine-modified Pn PS 19F and Bromoacetylated Tetanus Toxoid The N-(glycyl)cysteamine-modified Pn PS 19F (11.5 mg) was mixed with BrAc-TTd (5 mg), at a PS/TTd molar ratio of 7:1 at room temperature. Conjugation was monitored by GP-HPLC analysis (Shodex OHpak KB-805 and 804 in series, with PBS as eluent, 1 ml/min, at 35° C.). After ~110 h, the remaining thiol groups on the PS were capped with a 10-fold molar excess of bromoacetamide (based on the initial amino group content, as measured on the PS before reduction), for 6 h at room temperature. The remaining bromoacetyl groups on BrAc-TTd were capped with a 2.5-fold molar excess of 2-aminoethanethiol (based on the amount of bromoacetamide added previously) overnight at room temperature. The conjugate was purified at room temperature by low-pressure GPC on a Sephacryl S-400 HR (Pharmacia) column (100×1.6 cm) using PBS as eluent at a flow-rate of 0.8 ml/min. The appropriate fractions (8 ml) were analysed for carbohydrate and protein content (anthrone and Lowry assays), sterile-filtered and stored at 4° C.

Example 3

Preparation of Pn PS 6B/TTd-conjugate Vaccine Using Cystamine

Partial Depolymerisation of Pn PS 6B

Pneumococcal polysaccharide serotype 6B (American type 26, ATCC, lot. no. 2008862; 107 mg, dry weight), was dissolved in 17 ml water and sonicated in periods of 15 min, for a total of 150 min, with a ¼" microtip (Branson Sonifier 250, output level 6, 50% duty cycle). The m.w. of the PS was reduced from ~1350 to 46 kDa (from ~2,000 to ~65 RU). The solution was filtered over an 0.45 µm membrane with 80% recovery of PS (Dubois assay).

Modification of Pn PS 6B (46 kD) with Cystamine

For the modification, 4 ml of PS 6B solution was mixed with an equal volume of 1 M sodium carbonate solution (pH ~12). The mixture was cooled to ~2° C. While stirring, 170 µl CNBr reagent (100 mg/ml in acetonitrile) was added. After 10 minutes of reaction, the solution was subjected to gel filtration over Sephadex G25M at ~4° C. (eluent: 0.2 M carbonate-bicarbonate buffer pH 9.25). The PS-containing fraction was mixed with 3.25 ml pre-cooled 0.5 M cystamine dihydrochloride in 0.2 M sodium carbonate-bicarbonate, pH 9.25. The pH dropped to 8.7, and was re-adjusted to pH 9.25 with 0.3 M sodium hydroxide. The mixture was kept at pH 9.25 for 1.5 hours, with pH corrections as needed. Thereafter, the sample was kept at ~4° C. overnight. The sample was buffer-exchanged against 0.1 M sodium phosphate buffer, containing 5 mM EDTA, pH 8, and then concentrated to a volume of 2.2 ml on a Centriprep-10 (Amicon) concentrator. Analysis of primary amino groups gave 1 $NH_2$/3 RU (TNBS assay).

Reduction of Cystamine-modified Pn PS 6B

Cystamine-modified Pn PS 6B (16 mg in 0.1 M sodium phosphate buffer, containing 5 mM EDTA, pH 8) was reduced by adding a 10-fold molar excess of DTE (based on amino groups measured on the PS). After incubation overnight at room temperature, the sample was buffer-exchanged against 0.1 M sodium phosphate buffer, containing 5 mM EDTA, pH 7, and concentrated to a volume of 1.8 ml on a Centriprep-10. Analysis for sulphydryl groups gave 1 SH/8 RU (Ellman assay).

Bromoacetylation of Tetanus Toxoid

Tetanus toxoid (RIVM) was buffer-exchanged by gel filtration over Sephadex G25M (eluent: 0.1 M sodium phosphate buffer, containing 5 mM EDTA, pH 8). Amino groups of side-chains of lysine in the protein were modified by adding a 6-fold excess (based on the number of lysines within TTd) of BrAc-ONSu. The mixture was incubated for 2 h at room temperature and loaded onto a column of Sephadex G25M (eluent: 0.1 M sodium phosphate buffer, containing 5 mM EDTA, pH 7). Analysis of the protein-containing fraction showed that 55% of all the NH$_2$ groups had been modified (TNBS assay).

Conjugation of Cysteamine-modified Pn PS 6B and Bromoacetylated Tetanus Toxoid

The cysteamine-modified Pn PS 6B (12 mg) was mixed with BrAc-TTd (5 mg), at a PS/TTd molar ratio of 7.5:1 at room temperature. Conjugation was monitored by GP-HPLC analysis (Shodex OHpak KB-805 and 804 in series, with PBS as eluent, 1 ml/min, at 35° C.). After 91 h, the remaining thiol groups on the PS were capped with a 10-fold molar excess of bromoacetamide (based on the initial amino group content, as measured on the PS before reduction) for 6 h at room temperature. The remaining bromoacetyl groups on BrAc-TTd were capped with a 2.5-fold molar excess of 2-aminoethanethiol (based on the amount of bromoacetamide added previously) overnight at room temperature. The conjugate was purified at room temperature by low-pressure GPC on a Sephacryl S-400 HR (Pharmacia) column (100×1.6 cm) using PBS as eluent at a flow rate of 0.8 ml/min. The appropriate fractions (8 ml) were analysed for carbohydrate and protein content (Dubois and Lowry assays), sterile-filtered and stored at 4° C.

What is claimed is:

1. Method of covalently coupling a polysaccharide to a biopolymer having hydroxyl, amino and/or mercapto groups, the method comprising activating the polysaccharide with cyanogen bromide and subsequently reacting the activated polysaccharide with an aminothiol linker having the formula 1:

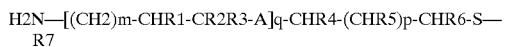

wherein

A is a direct bond or a group having the formula

m is an integer from 0 to 5;
n is an integer from 0 to 3;
p is an integer from 0 to 2;
q is the integer 0 or 1;
R1 is hydrogen or C1–C6 alkyl, wherein the C1–C6 alkyl is optionally substituted by amino, hydroxyl, carboxyl, C1–C4 alkoxycarbonyl, carbamoyl, mono- or di-C1–C4-alkylcarbamoyl or N-(α-carboxyalkyl) carbamoyl,; or, if m≠0, R1 is hydroxyl, amino or peptidyl-amino;
R2 and R3 are independently hydrogen or C1–C4 alkyl, or together from an oxo group; R4 is hydrogen, C1–C4 alkyl, carboxly, C1–C4 alkoxycarbonyl, carbamoly, mono-or di-C1–C4-alkylcarbamoyl or N-(α-carboxyalkyl) carbamoyl;
R5 is hydrogen, methyl, hydroxy or C1–C7 acyloxy;
R6 is hydrogen or methyl;
R7 is hydrogen or thiol-protecting group or group having the formula

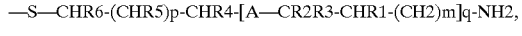

and

Z is imino, methylimino, oxygen or sulphur;
to produce a thiolated polysaccharide having the formula 2

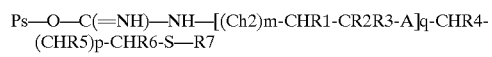

wherein Ps represents a polysaccharide residue and A, m, p, q, R1, R2, R3, R4, R5, R6 and R7 are as defined above, and reacting the thiolated polysaccharide with the biopolymer.

2. Method of covalently coupling a polysaccharide to a biopolymer having hydroxyl, amino and/or mercapto groups, the method comprising coupling said polysaccharide to an amino-thiol linker represented by the following formula:

wherein A, m, p, R1, R2, R3, R4, R5, R6 and R7 are as defined in claim 1, to produce an amino-thiol-linked polysaccharide and coupling said amino-thiol-linked polysaccharide to said biopolymer.

3. Method according to claim 1, wherein R$^7$ is a group having the formula

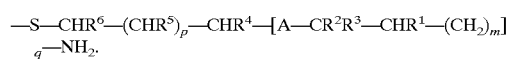

4. Method according to claim 1, wherein said thiol-protecting group R$^7$ is acyl, thioacyl or iminoacyl group such as —C(=O)—R, —C(=NR)—R, —C(=O)—SR, —C(=S)—NHR, —SO$_2$—OR or —P(=O)(OR$_2$), wherein R represents hydrogen or C$_1$–C$_7$ hydrocarbyl, optionally methyl, ethyl, allyl, tert-butyl, phenyl or benzyl.

5. Method according to claim 1, wherein R$^1$ represents the side chain of an α-amino acid, hydrogen, C$_1$–C$_4$ alkyl or α-hydroxyl C$_1$–C$_4$ alkyl.

6. Method according to claim 1, wherein R$^2$ and R$^3$ together form an oxo group.

7. Method according to claim 1, wherein A is a group having the formula —(NH—CHR$^1$—CO)$_n$NH—, and wherein n is an integer from 0 to 2.

8. Method according to claim 1, wherein R$^4$ and R$^5$ are hydrogen or methyl, hydrogen, and p=0 or 1.

9. A conjugate of two biopolymers, each having hydroxyl, amino and/or mercapto groups, covalently linked by a linking group having the formula:

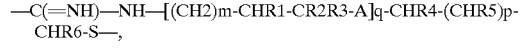

wherein

A is a direct bond or a group having the formula

wherein n is an integer from 0 to 2; or

m is an integer from 0 to 5;
n is an integer from 0 to 3;
p is an integer from 0 to 2;
q is the integer 0 or 1;
R1 is hydrogen or C1–C6 alkyl, wherein the C1–C6 alkyl is optionally substituted by amino, hydroxyl, carboxyl, C1–C4 alkoxycarbonyl, carbamoyl, mono- or di-C1–C4-alkylcarbamoyl or N-(α-carboxyalkyl)

carbamoyl; or, if m≠0, R1 is hydroxyl, amino or peptidyl-amino, or represents the side chain of an α-amino acid;

R2 and R3 are independently hydrogen or C1–C4 alkyl, or together from an oxo group;

R4 is hydrogen, methyl, C1–C4 alkyl, carboxly, C1–C4 alkoxycarbonyl, carbamoly, mono-or di-C1–C4alkylcarbamoyl or N-(α-carboxyalkyl) carbamoyl;

R5 is hydrogen, methyl, hydroxy or C1–C7 acyloxy;

R6 is hydrogen or methyl; and wherein

Z is imino, methylimino, oxygen or sulphur.

10. A conjugate of two biopolymers according to claim 9 wherein the linking group has the formula —HN—(CH$_2$)$_m$—CHR$^1$—CR$^2$R$^3$—A—CHR$^4$—(CHR$^5$)$_p$—CHR$^6$—S—;

wherein A, m, p, q, R$^1$, R$^2$, R$^3$, R$^4$, R$^5$ and R$^6$ are as defined in claim 9.

11. A conjugate according to claim 10, wherein said two biopolymers are respectively a polysaccharide and a peptide or protein.

12. A vaccine containing a conjugate according to claim 9.

13. Method according to claim 2, wherein R$^7$ is a group having the formula —S—CHR$^6$—(CHR$^5$)$_p$—CHR$^4$—[A—CR$^2$R$^3$—CHR$^1$—(CH$_2$)m]q-NH$_2$.

14. Method according to claim 2, wherein said thiol-protecting group R$^7$ is an acyl, thioacyl or iminoacyl group, optionally —C(=O)—R, —C(=S)—R, —C(=NR)—R, —C(=O)—SR, —C(=S)—NHR, —SO$_2$—OR or —P(=O)(OR)$_2$, wherein R represents hydrogen or C$_1$–C$_7$ hydrocarbyl.

15. Method according to claim 2, wherein R$^1$ represents the side chain of an α-amino acid, hydrogen, C$_1$–C$_4$ alkyl or α-hydroxy C$_1$–C$_4$ alkyl.

16. Method according to claim 2, wherein R$^2$ and R$^3$ together form an oxo group.

17. Method according to claim 2, wherein A is a group having the formula —(NH—CHR$^1$—CO)$_n$NH—, wherein n is an integer from 0 to 2.

18. Method according to claim 1, wherein R4 and R5 are hydrogen or methyl, hydrogen, and p=0 or 1.

19. Conjugate according to claim 10 wherein at least one of the two biopolymers comprise a polysaccharide linked to the terminal amino group of linking agent and a protein linked to the terminal thiol group of linking agent.

20. A method of preparing an immunogenic polysaccharide-biopolymer complex comprising activating a polysaccharide with a cyanating agent to provide polysaccharide isocyanate groups for coupling said polysaccharide to a biopolymer having hydroxyl, amino and/or mercapto groups, with a linking agent, wherein the linking agent has a basic nitrogen atom available for coupling to the polysaccharide and for coupling to the biopolymer, and a thiol group, said thiol group being optionally a protected thiol group.

21. A method according to claim 20 wherein the polysaccharide is activated with a cyanogen halide.

22. A method according to claim 5 or 15 wherein said side chain of an α-amino acid is a hydrogen, C$_1$–C$_4$ alkyl or α-hydroxyl C$_1$–C$_4$ alkyl.

23. A method of covalently coupling a polysaccharide to a biopolymer as claimed in claim 1 wherein the biopolymer is an activated biopolymer, said activated biopolymer being activated by N-succinimidyl-bromoacetate, N-(w-maleimidoalkyloxy)succinimide, cyanogen halide, carbodiimide, by introduction of an aldehyde group, by oxidation or by peptide synthesis with a biopolymer having an available carboxyl or amino group using one or more amino acid precursors containing an active function.

24. Method of covalently coupling a biopolymer having hydroxyl, amino and/or mercapto groups, to another biopolymer having hydroxyl, amino and/or mercapto groups, the method comprising (a) activating said first biopolymer with an activator; and (b) subsequently reacting the activated biopolymer with a linker having the formula:

—C(=NH)—NH—[(CH2)m-CHR1-CR2R3-A]q-CHR4-(CHR5)p-CHR6-S—,

—HN—(CH2)m-CHR1-CR2R3-A—CHR4-(CHR5)p-CHR6-S—,

H2N—[(CH2)m-CHR1-CR2R3-A]q-CHR4-(CHR5)p-CHR6-S—R7, or

H2N—(CH2)m-CHR1-CR2R3-A—CHR4-(CHR5)p-CHR6-S—R7 wherein each biopolymer independently is a natural or modified polysaccharide, a natural, modified or synthetic peptide, a protein, lipoprotein, glycoprotein or nucleic acid; said activation is effected by N-succinimidyl-bromoacetate, N-(w-maleimidoalkyloxy)succinimide, cyanogen halide, carbodiimide, by introduction of an aldehyde group, oxidation or by peptide synthesis using one or more amino acid precursors containing an active function;

wherein A is a direct bond or a group having the formula

—(NH—CHR1-CO)nNH—, wherein n is an integer from 0 to 2; or

—{Z—(CH2)m-CHR1-CHR2R3}nZ—;

m is an integer from 0 to 5;
n is an integer from 0 to 3;
p is an integer from 0 to 2;
q is the integer 0 or 1;
R1 is hydrogen or C1–C6 alkyl, wherein the C1–C6 alkyl is optionally substituted by amino, hydroxyl, carboxyl, C1–C4 alkcoxycarbonyl, carbamoyl, mono- or di-C1–C4-alkylcarbamoyl or N-(α-carboxyalkyl)carbamoyl; or, if m≠0, R1 is hydroxyl, amino or peptidyl-amino, or represents the side chain of an α-amino acid;

R2 and R3 are independently hydrogen or C1–C4 alkyl, or together from an oxo group;

R4 is hydrogen, methyl, C1–C4 alkyl, carboxly, C1–C4 alkoxycarbonyl, carbamoly, mono-or di- C1–C4-alkylcarbamoyl or N-(α-carboxyalkyl) carbamoyl;

R5 is hydrogen, methyl, hydroxy or C1–C7 acyloxy;

R6 is hydrogen or methyl;

R7 is hydrogen or thiol-protecting group or group having the formula

—S—CHR6-(CHR5)p-CHR4-[A—CR2R3-CHR1-(CH2)m]q-NH2,

—S—CHR6-(CHR5)p-CHR4-[A—CR2R3-CHR1-(CH2)m]q-NH2, or

—C(=O)—R,—C(=NR)—R,—C(=O)—SR;—C(=S)—NHR;—SO2-OR or —P(=O)(OR2), wherein R represents hydrogen or C1–C7 hydrocarbyl; and wherein Z is imino, methylimino, oxygen or sulphur; and (c) reacting the activated biopolymer which has been reacted with a linker with said other biopolymner.

25. A method of covalently coupling a polysaccharide to a biopolymer as claimed in claim 1 further comprising removing the protecting group $R^7$.

26. A method of covalently coupling a polysaccharide to a biopolymer as claimed in claim 23 further comprising removing the protecting group $R^7$.

* * * * *